(12) United States Patent
McCullagh et al.

(10) Patent No.: US 9,339,326 B2
(45) Date of Patent: May 17, 2016

(54) DIAMOND-LIKE CARBON ELECTRODE COATING

(75) Inventors: Orla McCullagh, Maynard, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2434 days.

(21) Appl. No.: 11/417,842

(22) Filed: May 3, 2006

(65) Prior Publication Data

US 2007/0260234 A1    Nov. 8, 2007

(51) Int. Cl.
*A61B 18/14* (2006.01)
*A61B 18/00* (2006.01)

(52) U.S. Cl.
CPC .......... *A61B 18/14* (2013.01); *A61B 2018/0016* (2013.01); *A61B 2018/00107* (2013.01); *A61B 2018/00577* (2013.01); *A61B 2018/1425* (2013.01)

(58) Field of Classification Search
CPC ..................... A61B 18/14; A61B 2018/00107; A61B 2018/0016; A61B 2018/00577; A61B 2018/1425

USPC ............................ 606/41, 45; 427/249.7, 902
See application file for complete search history.

(56) References Cited

U.S. PATENT DOCUMENTS

| 5,635,243 | A | * | 6/1997 | Turchan et al. ............ 427/248.1 |
| 5,795,648 | A | * | 8/1998 | Goel et al. .................... 428/336 |
| 2002/0072746 | A1 | * | 6/2002 | Lingenfelder et al. .......... 606/51 |
| 2003/0130653 | A1 | * | 7/2003 | Sixto et al. ....................... 606/45 |
| 2004/0181215 | A1 | * | 9/2004 | Kelly et al. ...................... 606/41 |

FOREIGN PATENT DOCUMENTS

| WO | 99/40858 | 8/1999 |
| WO | 01/50964 | 7/2001 |

* cited by examiner

*Primary Examiner* — Michael Peffley
*Assistant Examiner* — Samantha Good
(74) *Attorney, Agent, or Firm* — Kacvinsky Daisak Bluni PLLC

(57) ABSTRACT

An RF ablation device comprises an electrode including a DLC coating deposited on at least a portion thereof. A method of forming an RF ablation device, comprises forming a DLC coating on a portion of a metallic electrode.

15 Claims, 1 Drawing Sheet

DIAMOND-LIKE CARBON ELECTRODE COATING

BACKGROUND INFORMATION

Ablation is often the recommended treatment for certain fibroids, tumors or other tissue masses. For example, local ablation may be carried out by inserting a therapeutic device into target tissue and carrying out a therapeutic activity designed to destroy the tissue's cells. In one case, electrical energy may be applied to the affected area by placing one or more electrodes into the target tissue and discharging electric current therefrom to ablate the tissue. Alternatively, fluids with appropriate properties may be injected into the vicinity to chemically necrose the target tissue.

When RF energy is used to ablate tissue, the size and shape of the region of tissue ablated depends in part on the configuration of the electrodes and on the strength of the RF charge imparted to the target tissue. The energy applied to the tissue dissipates very rapidly with distance from the electrodes. Thus it is difficult to maintain the high level of energy density required to sufficiently ablate tissue across a large tissue volume. Therefore, ablating large portions of tissue often necessitates multiple applications of the ablation electrodes at various locations within a target tissue mass. High conductivity electrodes have been employed to improve the efficiency of these procedure and low friction electrodes have been employed to facilitate insertion and removal of the electrodes.

The energy transferred from electrodes to tissue declines as tissue adjacent to the electrodes becomes desiccated and loses its conductivity. This desiccated tissue surrounding the electrodes acts as an insulator preventing RF energy from reaching tissue separated from the electrodes by this insulative, desiccated tissue. As the tissue becomes desiccated, it often sticks to the electrodes making repositioning of the electrodes more difficult and time consuming.

SUMMARY OF THE INVENTION

In one aspect, the present invention is directed to an electrode for an RF ablation system, comprising a diamond-like carbon ("DLC") coating deposited on at least a portion thereof and a method of forming an RF ablation device comprising forming a DLC coating on a portion of a metallic electrode.

DETAILED DESCRIPTION

Figure 1:
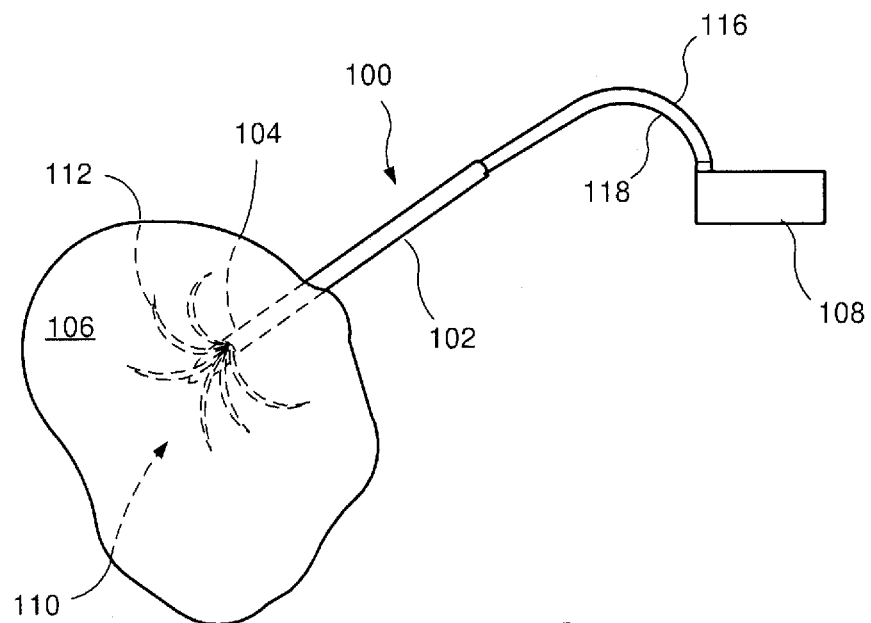
FIG. 1 shows a diagram of a tissue ablation system according to an embodiment of the present invention.

The present invention may be further understood with reference to the following description and the appended drawings, wherein like elements are referred to with the same reference numerals. Embodiments of the present invention relate to methods and systems for ablating target tissues. In particular, the embodiments are related to coatings for devices used in monopolar or bipolar RF ablation.

RF ablation devices typically fall into one of two broad categories. Monopolar systems insert electrodes of only one polarity to the target site while employing an external grounding pad or other similar device on the skin to provide a return path for the RF energy. A "loop" is thus formed extending from the (usually positive) electrode through the target tissue and the intervening tissue to the (usually negative) pad. With a bipolar system both positive and negative electrodes are inserted to the target site so that energy travels through the intervening tissue between electrodes of opposite polarities. Bipolar systems are generally more efficient as a stronger concentration of energy may be delivered to the target tissue which is preferably located between the positive and negative electrodes. Bipolar systems also provide greater control of the shape of the ablation region via the shaping and positioning of the electrodes.

Conventional needle-based radio frequency (RF) devices include, for example, the LeVeen Needle Electrode™ from the Oncology Division of Boston Scientific Corp. and the Starburst™ product line available from RITA Medical Systems, Inc. When using these devices, the surgeon punctures the target tissue mass with the device's needle, and then deploys one or more RF tines into the tissue mass to act as electrodes. A voltage is then applied to the array of tines to ablate the target tissue. Those skilled in the art will understand that lower levels of energy may be applied to achieve therapeutic goals other than destruction of the target tissue.

Great skill is often required to use these RF ablation devices because a target tissue mass may be only loosely held in place by ligaments or connective tissues and may move as the surgeon attempts to puncture it with the needle. Multiple attempts may be required before the needle is positioned correctly, prolonging the procedure and consuming valuable surgeon time. A grasping device such as a tumor screw may be used to immobilize and apply traction to the target tissue while the needle is inserted. This approach simplifies insertion of the needle into the tissue, but increases the complexity of the overall procedure, especially if multiple entry points through the skin are used to position the grasping device and the needle. Moreover, these procedures require the surgeon to manipulate multiple devices simultaneously, and may require the assistance of other personnel.

Several problems are common to both monopolar and bipolar systems. For example, as described above, the electrical coupling between target tissue and an electrode tends to degrade over time as tissue becomes desiccated and less conductive blocking the transmission of energy to tissue further away. This phenomenon can significantly limit the size of a region of tissue which may be ablated at a given level of RF energy.

The present invention reduces the effects of this phenomenon by transferring energy more evenly across a surface of an electrode to reduce or eliminate the effect of concentrated "hot spots" (e.g., a tip of the electrode). For example, a more even temperature distribution is obtained using an electrode formed of a heat conductor, such as a heat pipe. In addition, a heat conductive coating may be applied to areas which might otherwise concentrate heat to further even the temperature distribution. Applying a more even temperature distribution over a larger surface area allows a larger volume of tissue to be ablated for a given RF energy level as the desiccation of a small portion of tissue adjacent to a hot spot no longer electrically insulates the electrode from the target tissue.

In addition, as described above, tissue may stick to an electrode, especially as the tissue becomes desiccated and/or charred, hampering removal or repositioning of the electrode. Metal electrodes are most susceptible to this problem. In addition, this tissue may be pulled or torn as the electrodes are being re-positioned, increasing patient discomfort and the likelihood of infection and other complications.

These electrodes must be sharp to penetrate target tissues due to their density, composition, and/or lack of a solid backing against which to push. However, coatings applied to conventional electrodes have increased the thickness and softness of the electrodes, reducing their sharpness. This has been particularly true in the case of electrodes formed as arrays of tines because simultaneous deployment of the tines into target tissue in different directions can encounter high resistance from the tissue.

In addition, known coatings (e.g., anti-charring coatings) may further degrade the performance of the ablation electrodes by reducing conductivity or reducing tip hardness. However, exemplary embodiments according to the invention, show an RF ablation device with electrodes coated with materials improving anti-charring and anti-sticking properties, thermal conductivity and tissue penetration.

FIG. 1 shows an exemplary embodiment of an RF ablation device 100 according to the present invention including a cannula 102 and an array of tines 110 similar to those found in the LeVeen Needle Electrode™ ablation system. Those skilled in the art will understand that various embodiments of the present invention may be used in conjunction with different types of RF electrodes, and in particular with RF electrodes used to pierce tissue. In the exemplary embodiment depicted in FIG. 1, the array of tines 110 comprises a plurality of individual electrodes 112 which are deployable into target tissue 106. The cannula 102 also includes a sharp tip 114, shown in FIG. 2, to facilitate the insertion of the distal portion 104 into the target tissue 106. In a bipolar electrode configuration, an RF frequency generation apparatus 108 is preferably connected to the electrodes 112 by connectors 116, 118.

The distal tip 104 of the cannula 102 is inserted to a location within or adjacent to a target tissue mass 106 using, for example, ultrasound, fluoroscopy, a CT scanner or another visualization method. Once the cannula 102 has been properly positioned, the electrodes 112 are deployed and RF energy is delivered to the target tissue mass 106. Ionic agitation in the immediate vicinity of the electrodes 112 of the array of tines 110 generates frictional heating causing the tissue to coagulate and necrose. This ablating effect begins at the tips of the tines forming the electrodes 112 and propagates along the surfaces of the electrodes 112. From there, tissue necrosis propagates outward, forming a substantially spherical mass of ablated tissue surrounding the array of tines 110.

In one exemplary embodiment of the present invention, a thermally and electrically conductive coating of Diamond-like Carbon (DLC) is applied principally to the surface of the device's electrodes 112 as well as to other components of the RF ablation device 100 to improve anti charring, anti-sticking and thermal conductivity properties of the device as compared to a device having an un-coated metal cannula 102 and un-coated metal electrodes 112.

Diamond-like Coatings are amorphous carbon based coatings with a high hardness and a low coefficient of friction. Their unique composition and structure results in excellent wear resistance and non-sticking characteristics. These coatings are thin, chemically inert and have a low surface roughness. They can be tailored to have a wide range of electrical resistivity. The standard thickness of these layers is situated between 0.002 and 0.004 mm. DLC coatings are a mixture of sp2 and sp3 bonded carbon atoms with a hydrogen concentration between 0-80%.

As would be understood by those skilled in the art, diamond, a highly crystalline form of carbon, is the hardest naturally occurring material known. It was initially believed that diamond was unique from other forms of carbon because of its three dimensional tetrahedral atomic configuration. However, this belief was contradicted in 1971 by Aisenburg and Chabot, when they reported a film deposition technique which resulted in deposited thin layers of carbon having properties similar to those of diamond. The film produced according to the described technique was able to scratch glass, was highly insulating, had transparency, an index of refraction and a dielectric constant similar to those of diamond. For example, the index of refraction of the film was greater than 2, and the dielectric constant was between 8 and 14, compared to diamond's dielectric constant of 16.5. In one exemplary procedure, the coating could be grown on a substrate at room temperature using an ion-beam deposition technique, in which ion-beams are accelerated towards the substrate. In this method, the kinetic energy of the ion-beam facilitates growth of the thin film of insulating carbon.

Another form of carbon coating was developed in the 1940's, when chemical vapor deposition (CVD) techniques were used to energize a hydrocarbon gas mixture in a low pressure reaction generator, to deposit the diamond coatings. This procedure was not ideal, however, because excess graphite had to be removed from the coating, which required a lengthy and costly processing. For example, adding hydrogen to the gas mixture could be used to remove the graphite. Coatings which contain graphite and diamond bonds have become known as Diamond-like Carbon (DLC) coatings. As would be understood by those skilled in the art, properties of DLC coatings may be significantly modified by varying the composition of the precursor gases used, the deposition time and other parameters, to obtain a coating having specific desired properties. In a preferred embodiment according to the present invention, a DLC coating is formed using a Nitrogen doped (C:H:N) carrier gas to deposit the coating. A DLC coating using a nitrogen doped carrier gas, may be made electrically conductive by controlling of the pressures, temperatures and duration of the deposition process. This is especially important for coatings to be used on electrodes of the RF ablation system, such as the array of tines 110. This facilitates passage of the RF energy into the target tissue 106 with minimal energy loss. As will be described below, it is also beneficial to form a coating which is a good conductor of heat. Although exact deposition parameters have not yet been determined, it is believed that a coating having a thickness between approximately 0.002 mm and 0.02 mm is believed to provide the desired properties (e.g., to create thermal conductivity layers small enough to be negligible). The total resistance required is less than 25.

Figure 2:
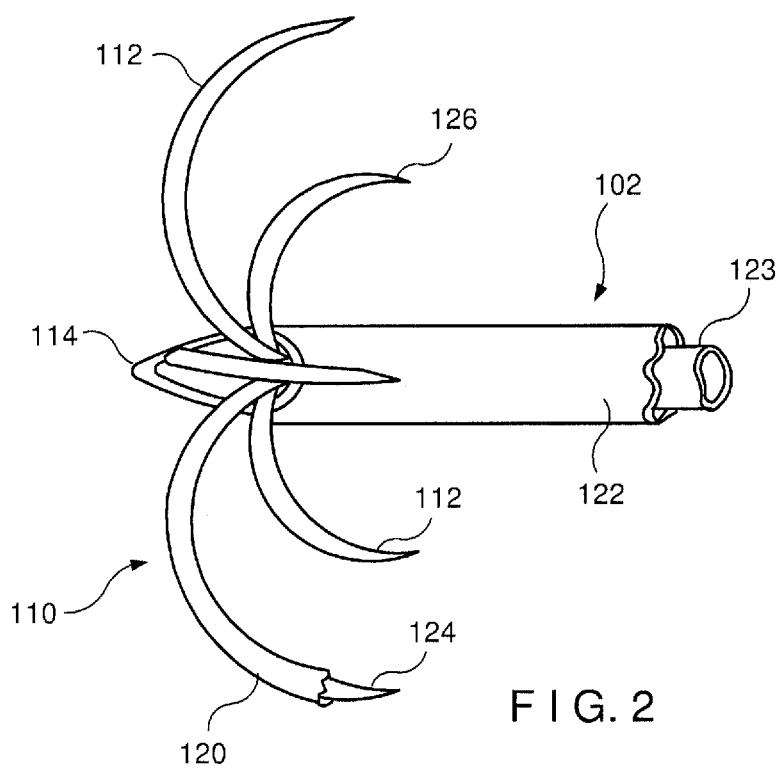
FIG. 2 shows a detailed diagram of RF electrodes with a DLC coating, according to the present invention.

With reference to FIG. 2, the exemplary embodiment of the invention comprises an array of tines 110 formed by coating a bare metal electrode 124 with a coating 120. In this embodiment, the coating 120 is a conductive layer of DLC. When deposited on the bare electrode 124, the coating 120 evens the temperature distribution along the surface of each of the electrodes 112, reducing charring. In addition, the lubricating qualities of the DLC coating reduce the sticking of the tissue 106 thereto. The smooth finish as well as the graphite containing composition of the DLC coating both contribute to its non-stick properties and this reduced sticking further reduces charring of the tissue in the immediate vicinity of the array of tines 110. That is, it has been observed that tissue sticking to the electrodes is much more likely to become charred and completely desiccated. DLC has a typical coefficient of friction of less than 0.1. It has been used for its lubricious properties in other industries, e.g. mold and tool surfaces.

As stated above, the DLC coating 120 also increases the thermal conductivity of the electrodes 112 resulting in a more even temperature distribution around the electrodes 112 and, consequently, within the target tissue mass 106. As described above, during conventional ablation procedures, the tissue adjacent to electrode tips is often heated disproportionately and may become fully desiccated. Providing a thermally conductive coating on the surface of the electrodes reduces the incidence of tissue charring by promoting a more uniform temperature of the tissue adjacent to the electrodes 112. The charring of the tissue adjacent to electrode tips associated with conventional ablation systems prohibits more aggressive heating sequences. However, the DCL coated electrodes 112 of the apparatus according to the present invention allow the desired ablation to be achieved more quickly through the use of a more aggressive heating sequence while avoiding the negative effects of premature tissue charring and desiccation. The coating prevents the tissue from adhering to the electrode improving the flow of power into the tissue rather than charring and building upon the layer of adhered tissue. In normal situations as the layer of adhered tissue builds, resistance increases, requiring a corresponding exponential increase in the impedance as the power drops to complete the ablation In addition, the DLC coating improves the ability of the electrodes 112 to penetrate tissue. As described above, DLC is low friction and reduces the drag experienced by the array of tines 110 as they are deployed from the cannula 102 into the target tissue mass 106. A similar reduction in drag is also experienced by the array of tines 110 during retraction into the cannula 102 after completion of the ablation procedure. In addition to reducing the friction between the electrodes 112 and the surrounding tissue, the DLC coating is also very hard and is able to retain a sharp edge. Thus, when the electrode 112 of the array of tines 110 is sharpened after receiving the DLC coating, the tips 126 of the electrodes 112 will be sharper as the case hardened DLC allows creation of a finer surface without burrs and which will resist developing ragged edges (similar to sharpened 300SS which is soft versus 440CSS which is high in C and allows you to form a sharper edge). The DLC coating allows the tines 110 to retain their sharpness.

In yet another embodiment according to the present invention, the ability of the array of tines 110 to penetrate the target tissue 106 may be further improved by shaping the DLC coating at the tips 126 of the electrodes 112. For example, the deposition of the coating may be carried out in such a way that the crystalline structure of the coating forms a cutting surface at the tip 126. As would be understood by those skilled in the art, the parameters governing the deposition of the coating 120 may be manipulated to obtain a desired shape and orientation of the deposited coating, so that a diamond edge is formed in the direction of electrode deployment into the tissue. This further facilitates insertion of the electrodes 112 by facilitating cutting through the target tissue mass 106 as the array of tines 110 is deployed from the cannula 102.

The DLC coating according to the present invention may be applied to either a single needle RF ablation system using one electrode, or to an array of electrodes, as depicted in the drawings. In either case, the more lubricious surface of the electrodes, the increased char-resistance and the greater ability to penetrate the target tissue conferred by the DLC coating results in a more effective, simpler to use ablation system. Although the above description is directed principally to a bipolar array probe, those skilled in the art will understand that the same benefits may be obtained by employing the DLC coating on a monopolar ablation system. In addition, it may be beneficial to apply the DLC coating to other portions of the RF ablation probe. For example, a coating 122 may be applied to a bare metal cannula 123, to facilitate penetration of tissue by the cannula 102 for insertion to a target location adjacent to the target tissue mass 106.

In a different embodiment according to the invention, DLC is used to form a coating with properties which vary, for example, along the length of the ablation probe or electrode, to form insulated and conductive regions. A tough and lubricious coating is applied to the entire device with the process parameters being varied during deposition as described above so that preselected portions of the device are coated with thermally and/or electrically insulative DLC. Using the DLC coating to provide insulation is beneficial because it eliminates the need to add thick, bulky insulation to the device. In addition or alternatively, semi-conductive portions of the electrodes and/or of the probe may be formed, for example by varying the process parameters during deposition to apply to these areas a coating of DLC with a dielectric constant lower than that of the insulative DLC and higher than that of the conductive DLC.

As an insulator the electrical resistivity may be $>10^{10}$ cm. This value may be modified as the precursor gases and deposition parameters are changed. The ranges of conductivity were discussed above but can be customized for other electrodes as required. As described above, the resistivity of a semi conductive material may be in a range greater than 25 and still be conductive.

The present invention has been described with reference to specific exemplary embodiments. Those skilled in the art will understand that changes may be made in details, particularly in matters of shape, size, material and arrangement of parts. Accordingly, various modifications and changes may be made to the embodiments. Additional or fewer components may be used, depending on the condition that is being treated by the RF ablation system. The specifications and drawings are, therefore, to be regarded in an illustrative rather than a restrictive sense.

What is claimed is:

1. An electrode for an RF ablation system, comprising a DLC coating containing graphite deposited on at least a portion thereof, the DLC coating including an electrically conductive region having a first dielectric constant and an electrically insulative region having a second dielectric constant, the first dielectric constant being less than the second dielectric constant.

2. The electrode according to claim 1, wherein a tissue penetrating distal tip of the electrode is formed of the DLC coating.

3. The electrode according to claim 1, wherein heat conduction and lubricious properties of the DLC coating are selected to minimize tissue charring.

4. An RF ablation device comprising:
   an elongated cannula adapted for insertion into a target tissue;
   an electrode deployable into the target tissue from the cannula; and
   a DLC coating containing graphite on a portion of the electrode, the DLC coating including a thermally conductive region and a thermally insulative region, a thermal conductivity of the DLC coating in the thermally conductive region being greater than a thermal conductivity of the DLC coating in the thermally insulative region.

5. The RF ablation device according to claim 4, wherein a tissue penetrating distal tip of the electrode is formed of the DLC coating.

6. The RF ablation device according to claim 4, wherein a portion of the cannula includes a DLC coating.

7. The RF ablation device according to claim 4, wherein the electrode comprises a plurality of DLC coated electrodes forming an array deployable from the cannula into target tissue.

8. The RF ablation device according to claim 4, wherein the DLC coating comprises an electrically conductive region having a first dielectric constant and an insulative region having a second dielectric constant, the first dielectric constant being less than the second dielectric constant.

9. The RF ablation device according to claim 8, further comprising a semi-conductive region in which a dielectric constant of the DLC coating is less than the second dielectric constant and greater than the first dielectric constant.

10. A method of forming an RF ablation device, comprising:
    forming a DLC coating containing graphite on a portion of a metallic electrode by deposition, controlling parameters of the deposition process to obtain, in a first electrically conductive region, DLC having a first dielectric constant and, in a second electrically insulative region, DLC having a second dielectric constant greater than the first dielectric constant.

11. The method according to claim 10, further comprising controlling parameters of the deposition process to obtain, in a third semi-conductive region, DLC having a third dielectric constant greater than the first dielectric constant and less than the second dielectric constant.

12. The method according to claim 10, further comprising controlling parameters of the deposition process to obtain, in a tissue penetrating location, DLC having at least a predetermined hardness.

13. The method according to claim 10, further comprising forming a coating of DLC on a portion of a cannula from which the electrode is deployed by deposition.

14. The method according to claim 13, further comprising controlling parameters of the deposition process so that the DLC coated on the portion of the cannula has at least a predetermined thermal conductivity.

15. The method according to claim 13, further comprising controlling parameters of the deposition process so that the DLC coated on the portion of the cannula has a coefficient of friction of no more than 0.1.

* * * * *